US00PP10546P

United States Patent [19]

Bjorge et al.

[11] Patent Number: Plant 10,546

[45] Date of Patent: Aug. 11, 1998

[54] 'FA 52' PEACH TREE

[75] Inventors: Annette Bjorge; Randy Bjorge, both of Coloma, Mich.

[73] Assignee: International Plant Management, Lawrence, Mich.

[21] Appl. No.: 738,679

[22] Filed: Oct. 28, 1996

[51] Int. Cl.[6] ..... A01H 5/00

[52] U.S. Cl. ..... Plt./43.1

[58] Field of Search ..... Plt./43.1

*Primary Examiner*—James R. Feyrer

[57] ABSTRACT

A new peach variety, *Prunus persica*, (hereinafter referred to as the 'FA 52' peach tree variety) which was developed by Annette and Randy Bjorge in a breeding program at Fruit Acres Farm in Coloma, Mich., having the following combination of unique and desirable features:

1. A fruit with excellent shipping and storage qualities.
2. A fruit maturing at the same time as the 'Redhaven' peach.
3. A substantially round fruit with semi-freestone, yellow flesh and an attractive red stripe over a medium red blush covering 80% of the fruit at maturity.
4. A fruit with flesh that does not brown when cut.
5. A tree and fruit with resistance to Bacterial Spot.
6. A tree and blossom with hardiness superior to its parent.

3 Drawing Sheets

ORIGIN OF THE VARIETY

The new variety of 'FA 52' peach tree was developed by Annette and Randy Bjorge in a peach breeding program at Fruit Acres Farms, 2559 Friday Road, Coloma, Mich. 49038. The 'FA 52' peach tree was developed as an open pollinated seedling of 'Newhaven', an established commercial variety. The parent tree was grown and is maintained in a peach tree breeding orchard in Fruit Acres Farms.

This new and distinct variety of peach tree has been asexually propagated by budding at Fruit Acres Farms in Coloma, Mich. The asexual propagation demonstrates that such reproduction of the characteristics of the tree are consistent and are established and transmitted through succeeding generations.

SUMMARY OF THE VARIETY

The new and distinct variety of peach tree is of low spreading growth with medium density and is regular and productive bearer of peaches. The fruit of the new variety is characterized by round, substantially 80% red fruits with a subtle striped color pattern that bleeds into a red blush that presents a very attractive appearance. The fruits have firm flesh and are resilient to the extent that they may be handled and packaged mechanically without damaging the same for shipment. This results in less spoilage and a greater market value. The flesh of the fruits of the new variety does not brown when cut. The fruits of the new variety have a recessed pistil point which avoids damage during picking and handling.

The tree and fruits of the new variety exhibit good resistance to Bacterial Spot and are very cold hardy. The fruit matures at the beginning of the peach growing season in Southwestern Michigan. It ripens concurrently with the established commercial variety, 'Redhaven'.

BRIEF DESCRIPTION OF THE PHOTOGRAPHS

The accompanying photographs show typical specimens of the new variety in color as nearly true as it is reasonably possible to make the same in color illustrations of this character. The specimens were photographed in Van Buren and Berrien counties of Southwestern Michigan.

FIG. 1. illustrates specimens of the fully ripened fruit and foliage of the new variety.

FIG. 2. illustrates blooms of the new variety.

FIG. 3. illustrates two specimens of the new variety. The upper specimen is bisected along the suture, the lower specimen is bisected as a ninety-degree angle to the plane of the suture. The color and forms of the flesh, pit and pit cavity are illustrated.

DETAILED DESCRIPTION OF THE VARIETY

Figure 1:
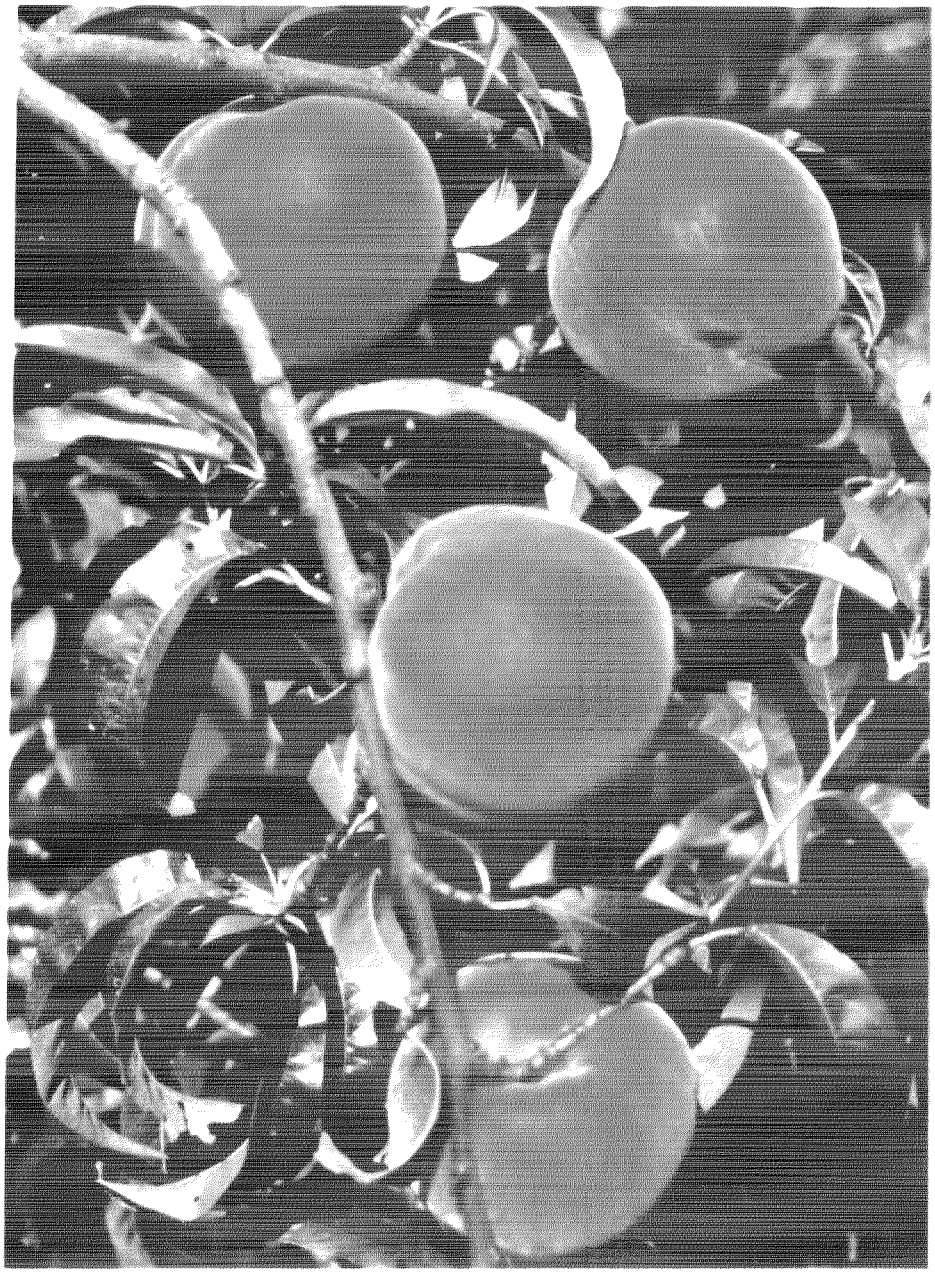
Figure 2:
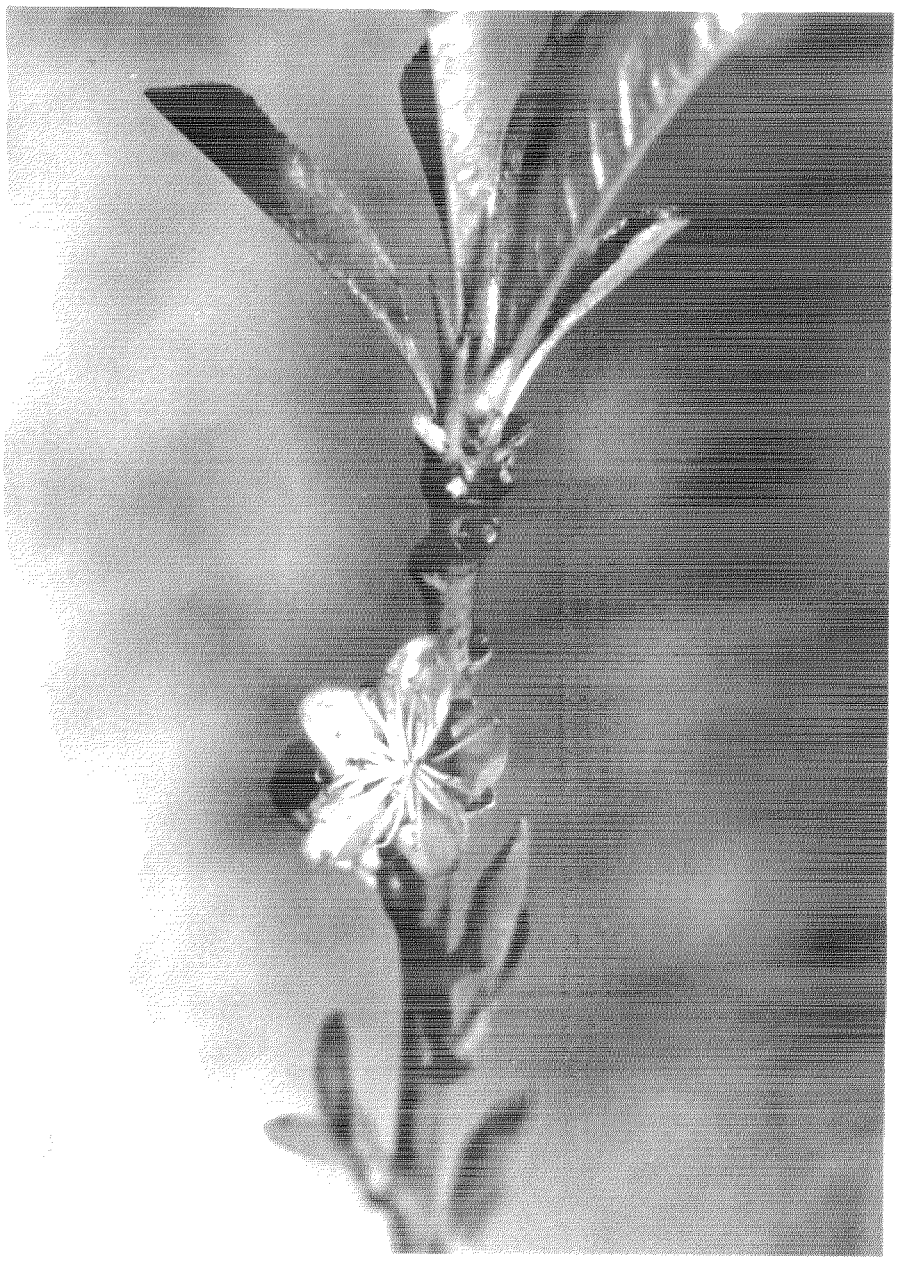
Figure 3:
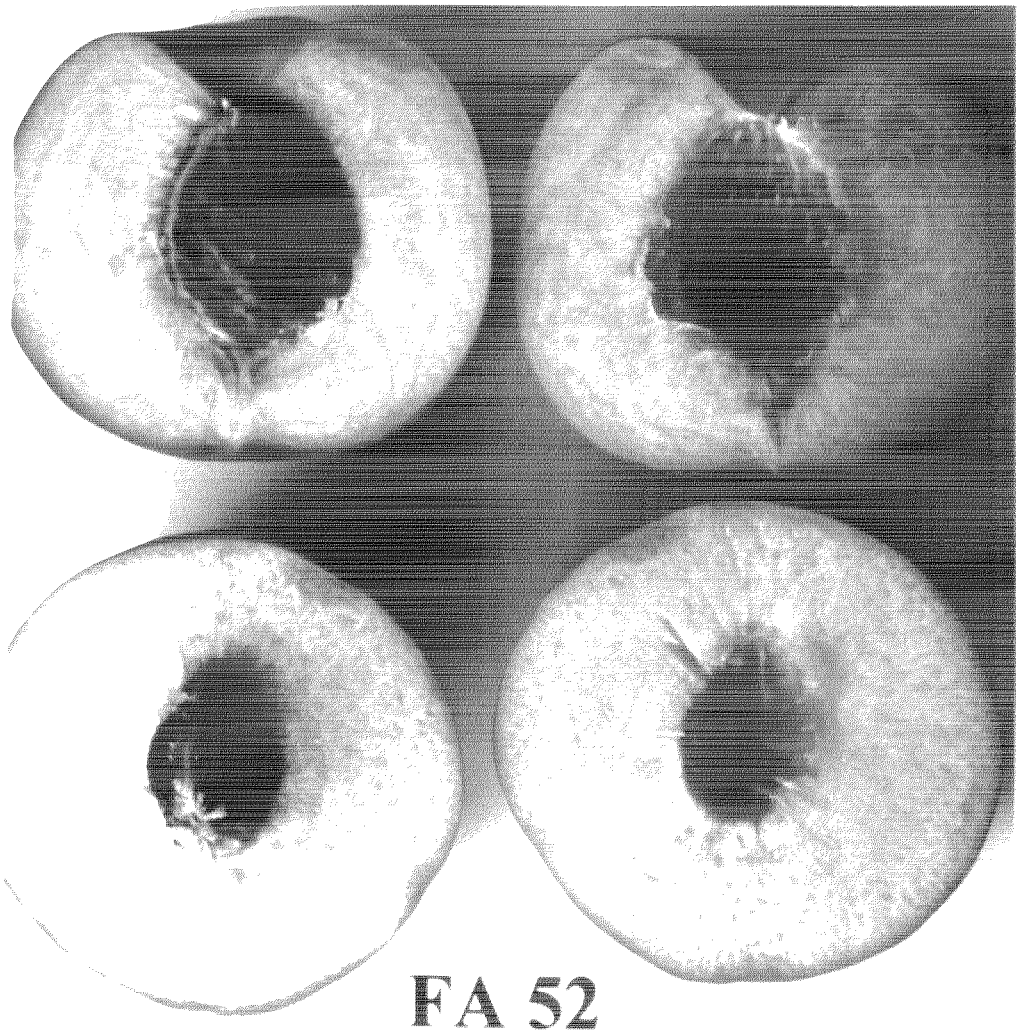

The following description of the fruit and foliage of the new variety is based on observations of specimens grown in Berrien and Van Buren County of southwestern Michigan. The color terminology is in accordance with The Royal Horticultural Society Colour Chart, published by The Royal Horticultural Society of London, England.

Tree:

*Age of specimen.*—15 years.

*Height.*—Unpruned 4.M.

*Width.*—Unpruned 4.6M.

*Size.*—Medium.

*Vigor.*—Vigorous, requires moderate thinning. Requires spring pruning.

*Density.*—Open, internode length is 1½ to 2 cm.

*Form.*—Spreading, major scaffold branches form a 50° to 60° angle to the trunk. Will form a central leader if left unpruned. Does not require supplemental support.

*Production.*—Very productive, ripens in 2 pickings with 70% of the crop mature for the first picking and 30% mature for the second picking. Productive capacity is similar to Redhaven. Is more productive that it's parent. Fruit will hold on the tree for 1 week at maturity.

*Bearing.*—Annual, harvest season last 4 days in a normal year.

*Disease resistance.*—Moderate resistance to bacterial spot.

*Cold hardiness.*—Very hardy.

Trunk:

*Size.*—Medium.

*Surface.*—Medium shaggy.

*Lenticils.*—Large.

*Color.*—Gray 201 A.

Leaves:

*Size.*—Length 180 mm, width 65 mm.

*Form.*—Lanceolate, pointed.

*Thickness.*—Medium.

*Texture.*—Medium.

*Margin.*—Crenate.

*Petiole.*—Length 12 mm.

*Glands.*—Rounded, number varies from 2 to 3, average 2, located at the base of leaf and the upper portion of petiole.

*Color.*—Upper surface Green 147 A, lower surface Green 147 B.

*Stipules*—None.

Flower buds:

*Size.*—Medium.

*Length.*—Medium.

Flowers:

*Blooming period.*—April 8 to 15 in Coloma, Mich.

*Presentation.*—Non-showy.

*Pollen.*—Present, self fertilizing.

*Petals.*—5 in number, small, slightly cupped, Red-Purple 73 A.

*Stamens.*—Curved at end.

*Pistil.*—Length 11 mm, White 155 A.

Fruit:

*Maturity when described.*—Firm ripe.

*Date of first picking.*—August 5 in Southwestern Michigan.

*Size.*—65 to 80 mm.

*Form.*—Round.

*Suture.*—Clean, some indentation.

*Pistil point.*—Inverted.

Skin:

*Thickness.*—Medium.

*Texture.*—Smooth.

*Tendency to crack.*—None.

*Down.*—Moderate.

*Color.*—A very attractive 80% Red 47A blush with a subtle, mottled stripe of Red 46 A over a background of Yellow-Orange 20A.

Flesh:

*Texture.*—Firm, melting when full ripe.

*Aroma.*—*Sweet, medium aroma.*

*Fibres.*—Few, small, tender, not conspicuous or noticeable in eating.

*Color.*—Yellow-Orange 23 C.

*Coloration at the pit.*—Clear yellow with occasional soft pink bleeding into the pit cavity.

*Eating quality.*—Excellent, high sweetness with medium acidity.

Stone:

*Size.*—Length 31 mm, width 24 mm, thickness 18 mm.

*Form.*—Ovate.

*Apex.*—Pointed.

*Sides.*—Nearly equal.

*Base.*—Slightly slanted.

*Surface.*—Pitted to furrowed throughout.

*Color.*—Grayed-Orange 166 A.

*Type.*—Semi-free, similar to 'Redhaven'.

*Tendency to crack.*—Slight.

Use: Desert, fresh market and commercial.

Shipping quality: Excellent.

Keeping quality: Excellent, will keep 3 weeks in common cold stoarge.

I claim:

1. A new and distinct variety of peach tree, *Prunus persica,* substantially as herein shown and described, characterized particularly as to novelty by the unique combination of medium size, very vigorous, spreading, very hardy, open, medium density, regular bearing tree, with resistance to bacterial spot, producing semi-freestone fruits having yellow, non-browning flesh and substantially round, firm, 80% striped red skin color at maturity which occurs concurrently with 'Redhaven' peach.

* * * * *

FA 52